(12) United States Patent
Saleh (10) Patent No.: US 11,439,348 B1
(45) Date of Patent: Sep. 13, 2022

(54) APPARATUS, SYSTEMS AND METHODS FOR AFFECTING THE PHYSIOLOGICAL CONDITION OF A USER

(71) Applicant: Lena Saleh, Charlotte, NC (US)

(72) Inventor: Lena Saleh, Charlotte, NC (US)

( * ) Notice: Subject to any disclaimer, the term of this patent is extended or adjusted under 35 U.S.C. 154(b) by 194 days.

(21) Appl. No.: 16/595,836

(22) Filed: Oct. 8, 2019

Related U.S. Application Data

(60) Provisional application No. 62/820,401, filed on Mar. 19, 2019.

(51) Int. Cl.
*A61B 5/00* (2006.01)

(52) U.S. Cl.
CPC .............. *A61B 5/68* (2013.01); *A61B 5/0022* (2013.01); *A61B 5/0059* (2013.01)

(58) Field of Classification Search
None
See application file for complete search history.

(56) References Cited

U.S. PATENT DOCUMENTS

| | | | | |
|---|---|---|---|---|
| 5,167,610 A | * | 12/1992 | Kitado | A61M 21/00 128/905 |
| 5,518,497 A | * | 5/1996 | Widjaja | A61M 21/00 600/26 |
| 6,212,135 B1 | * | 4/2001 | Schreiber | A63B 23/185 368/107 |
| 6,720,743 B2 | * | 4/2004 | Yano | H05B 39/044 315/291 |
| 8,562,511 B2 | * | 10/2013 | Haisma | A61M 21/00 600/27 |
| 9,610,035 B2 | * | 4/2017 | Aarts | A61B 5/18 |
| 10,195,377 B2 | * | 2/2019 | Asanoi | A61B 5/4812 |
| 10,278,638 B2 | * | 5/2019 | Dusanter | A61B 5/01 |
| 10,610,153 B2 | * | 4/2020 | Auphan | A61F 5/56 |
| 10,729,332 B2 | * | 8/2020 | Heneghan | A61B 5/0205 |

(Continued)

FOREIGN PATENT DOCUMENTS

CN  207768391 U  8/2018

OTHER PUBLICATIONS

Livlab, "What kind of insomniac are you" downloaded on Jan. 30, 2019, at: https://www.mydodow.com/dodow/en-us/home, pp. 1-12.

(Continued)

*Primary Examiner* — Shirley X Jian
(74) *Attorney, Agent, or Firm* — Additon, Pendleton & Witherspoon, P.A.

(57) ABSTRACT

A system for detecting and affecting the physiological condition of a user can include at least one non-contact sensor configured to detect at least one physiological condition of a user, and a device configured for affecting the user's environment. A controller can be configured to control operation of the device in response to signals from the sensor. The device can include a housing having an interior space, at least one light source positioned in the interior space, a window mounted to the housing and configured to allow light from the at least one light source to pass through the window and outwardly from the housing. Light can be emitted from the at least one light source so that brightness of the light changes through a time cycle that is serially repeated for guiding breathing of the user. The device can be independent of the system.

20 Claims, 5 Drawing Sheets

(56) References Cited

U.S. PATENT DOCUMENTS

| | | | | |
|---|---|---|---|---|
| 2004/0225340 | A1* | 11/2004 | Evans | A61M 21/00 607/88 |
| 2011/0015468 | A1* | 1/2011 | Aarts | A61B 5/486 600/26 |
| 2012/0029322 | A1* | 2/2012 | Wartena | A61B 5/398 600/301 |
| 2012/0125337 | A1* | 5/2012 | Asanoi | A61M 16/101 128/204.23 |
| 2014/0057232 | A1* | 2/2014 | Wetmore | A61N 1/36025 434/236 |
| 2015/0320588 | A1* | 11/2015 | Connor | A61F 7/0085 607/107 |
| 2016/0015314 | A1* | 1/2016 | Dusanter | A61B 5/0816 600/301 |
| 2016/0015315 | A1* | 1/2016 | Auphan | A61B 5/6892 600/301 |
| 2016/0151603 | A1* | 6/2016 | Shouldice | H04R 3/00 600/28 |
| 2018/0064402 | A1* | 3/2018 | Leydon | A61M 15/0021 |
| 2019/0290959 | A1* | 9/2019 | Chesbrough | A61M 21/02 |
| 2019/0320939 | A1* | 10/2019 | Orvis | A61B 5/0022 |
| 2020/0069891 | A1* | 3/2020 | Gupta | B05B 12/02 |
| 2020/0178892 | A1* | 6/2020 | Maslik | A61B 5/0205 |
| 2022/0061696 | A1* | 3/2022 | Tseng | A61B 5/0013 |

OTHER PUBLICATIONS

Pallesen et al., "A Pilot Study of Impulse Radio Ultra Wideband Radar Technology as a New Tool for Sleep Assessment", Journal of Clinical Sleep Medicine, Jul. 15, 2018, pp. 1-11.

Xethru, "An introduction to sleep monitoring using the X2M200 sensor", downloaded on Jan. 30, 2019, at: https://www.xethru.com/blog/posts/an-introduction-to-sleep-monitoring-using-the-x2m200-sensor, pp. 1-4.

Xethru, "High-end and Non-contact Sensor Technology for Respiration Monitoring" Dec. 3, 2014, pp. 1-11.

Xethru, "XeThru X2M200 Sleep Monitoring" Introduction to a Good Night's Sleep, Rev. A, Aug. 15, 2016, pp. 1-14.

Xethru, "XeThru vs. Polysomnograph (PSG) Comparative Study" v. 12, May 19, 2016, pp. 1-13.

Dezeen, "Future Sleep kit stops people looking at their phones before bed" downloaded (2017), at https://www.dezeen.com/2017/07/24/future-sleep-kit-stops-people-looking-at-phones-before-bed-design-graduates/, pp. 1-8.

OnOfice, "Wellness at work starts with a good night's sleep", (Oct. 10, 2018) downloaded from: https://www.onofficemagazine.com/design/item/5392-lena-saleh-zeitgeiber-kit-sleep, pp. 1-4.

Dodow, Scientific research data, (no dated) pp. 1-16.

Housley, "Natural light: The next wellness obsession", WGSN Insider, https://www.wgsn.com/blogs/natural-light-the-next-wellness-obsession/, Jul. 5, 2017, pp. 1-11.

\* cited by examiner

APPARATUS, SYSTEMS AND METHODS FOR AFFECTING THE PHYSIOLOGICAL CONDITION OF A USER

CROSS-REFERENCE TO PRIORITY APPLICATION

This application claims the benefit of U.S. Provisional Patent Application No. 62/820,401 for "Apparatus, Systems and Methods for Affecting the Physiological Condition of a User" (filed Mar. 19, 2019), which is hereby incorporated by reference in its entirety.

BACKGROUND

The present invention generally relates to devices for use in helping to positively control the psychological state of a user.

There is a desire for such devices that provide a new balance of properties

SUMMARY

An aspect of this disclosure is the provision of an apparatus for affecting the physiological condition of a user. The apparatus can include a housing having an interior space, at least one light source positioned in the interior space, a window mounted to the housing and configured to allow light from the at least one light source to pass through the window and outwardly from the housing, and a controller in communication with the at least one light source. The controller can be configured to provide first and second modes of operation. In the first mode, light is emitted from the at least one light source so that brightness of the light changes through a time cycle that is serially repeated for guided breathing of the user. In the second mode, color of the light emitted from the at least one light source is different than color of the light emitted from the at least one light source during the first mode. At least one switch can be in communication with the controller and configured to allow the user to select between at least the first mode and the second mode.

Another aspect of this disclosure is the provision of a system for detecting and affecting the physiological condition of a user. The system can include at least one non-contact sensor configured to detect at least one physiological condition of a user, a device configured for affecting the user's environment, and a controller configured to communicate with both the sensor and the device. The controller can be configured to control operation of the device and, thus, affect the user's environment in response to signals from the sensor. The device can be the above-mentioned apparatus, a diffusor, and/or other suitable device.

The foregoing summary provides a few brief examples and is not exhaustive, and the present invention is not limited to the foregoing examples. The foregoing examples, as well as other examples, are further explained in the following detailed description with reference to accompanying drawings

BRIEF DESCRIPTION OF THE DRAWINGS

The drawings are provided as examples, and they are typically schematic and may not be drawn to scale. The present invention may be embodied in many different forms and should not be construed as limited to the examples depicted in the drawings.

DETAILED DESCRIPTION

Examples of embodiments are disclosed in the following. The present invention may, however, be embodied in many different forms and should not be construed as limited to the embodiments set forth herein. For example, features disclosed as part of one embodiment or example can be used in the context of another embodiment or example to yield a further embodiment or example. As another example of the breadth of this disclosure, it is within the scope of this disclosure for one or more of the terms "substantially," "about," "approximately," and/or the like, to qualify each of the adjectives and adverbs of the Detailed Description section of disclosure, as discussed in greater detail below.

Figure 1:
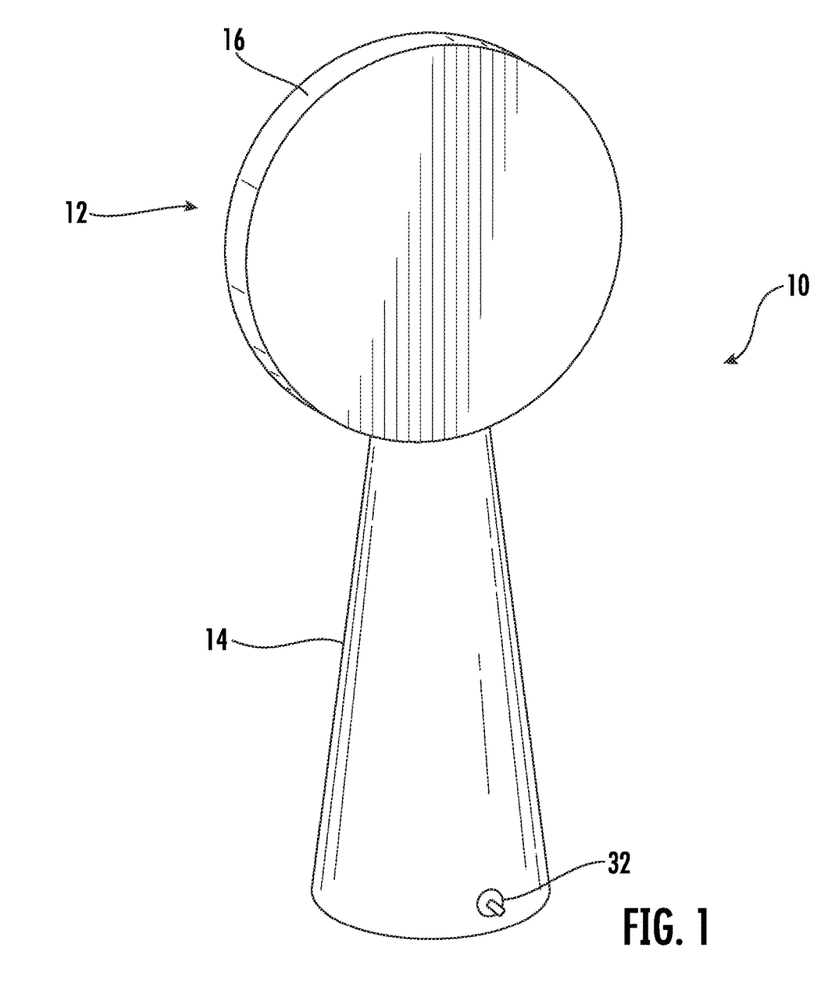
FIG. 1 is a front pictorial view of a unit configured to detect and/or positively affect the physiological condition of a user, in accordance with a first embodiment of this disclosure.

FIG. 1, depicts a unit 10 (e.g., "zeitgeber unit") configured to detect and/or affect one or more physiological conditions of a user, in accordance with a first embodiment of this disclosure. The physiological conditions can include one or more vital signs and/or the physiological state of the user. For example, the unit 10 can be configured to respectively promote sleep, wakefulness, and/or diaphragmatic or deep breathing. Diaphragmatic or deep breathing typically involves relatively slow and relatively deep inhalation, followed by relatively slow and relatively complete exhalation, as discussed in greater detail below.

Optionally, the unit 10 can be part of a networked system. In one example, the unit 10 and/or networked system includes at least one of each of a detector for detecting at least one physiological condition of the user, and a device for affecting the environment in which the user is located ("environment-affecting device"). In the first embodiment, the detector utilizes non-contact sensing to determine one or more indicators of the physiological condition of the user, and the detector outputs data representative of the indicators. The unit 10 and/or networked system typically further includes a computer, or the like, for processing the data from the detector, and responsively providing instructions to the environment-affecting device. The instructions and environment-affecting device are cooperatively configured in a manner that seeks to affect the physiological condition of the user in a predetermined manner (e.g., to respectively promote sleep, wakefulness, and/or diaphragmatic or deep breathing). The networked system will be discussed in greater detail below, following a detailed description of the unit 10.

In the first embodiment depicted in FIG. 1, the unit 10 is configured to sit on a surface (e.g., the top surface of a bedside table) so that an upper body 12 of the unit is within several feet or yards from a user, and a front face of the upper body is facing toward the user. In the example depicted in FIG. 1, the cylindrical upper body 12 is supported by an upright, frustoconical base 14.

Figure 2:
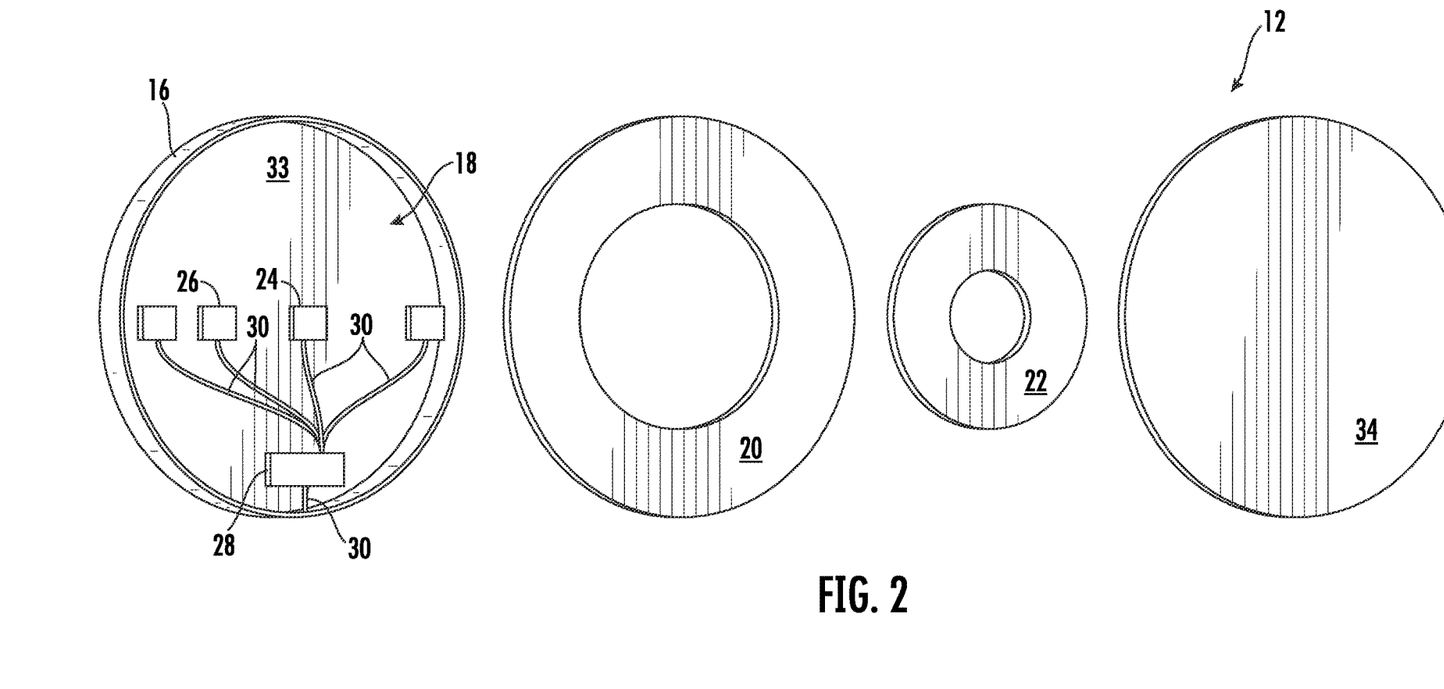
FIG. 2 is an isolated, exploded view of an upper body of the unit of FIG. 1, in accordance with the first embodiment.

Referring also to FIG. 2, the body 12 can include a cylindrical housing 16 at least partially forming a chamber having an interior space 18. The housing 16 can include a cylindrical, outer sidewall that extends around both the interior space 18 and a horizontal cylindrical axis. Alternatively, the unit 10 can be configured differently. For example, the cylindrical axis may be inclined. As further examples, the base 14 may be omitted and/or the body 12 may be in other suitable shapes that may include, for example, the shape of a truncated cylinder, a dome, a truncated dome, a vase, an obelisk, a sculpture, and/or other suitable shapes.

Referring also to FIG. 2, the first embodiment unit 10 includes electronic components that are mounted in the interior space 18 of the upper body 12. The unit's electronic components can include at least one light panel, for example an outer light panel 20 and an inner light panel 22. The unit's electronic components can further include a controller for controlling operation of the one or more light panels 20, 22. As an example, a digital computer 28 can control operation of the light panels 20, 22 by way of a suitable output adapter. The computer 28 can have associated therewith and/or may be replaced by one or more programmable logic devices (PLDs) and/or application-specific integrated circuits (ASIC), as will be discussed in greater detail below.

As a further example, the unit's electronic components can include at least one sensor, or more specifically a detector (e.g., radar system) including at least one non-contact sensor, as will be discussed in greater detail below. Also discussed in greater detail below, the unit's electronic components can include a network communication adapter 26. The electronic components 20, 22, 24, 26, 28 can be mounted in the housing interior 18 and respectively be in electrical communication by way of electrical wiring 30 and/or in any other suitable manner. Whereas the electronic components 20, 22, 24, 26, 28, 30 are schematically depicted as being separate features in FIG. 2, they may be more closely associated with one another, for example by being incorporated onto (e.g., being mounted on) one or more printed circuit boards and/or being part of one or more integrated circuits.

The unit 10 can further include a variety of differently user interface. In the example depicted in FIG. 1, the unit 10 includes at least one relatively simple type of user interface in the form of a manually operable, push-button-actuated switch 32 mounted to the base 14, or in any other suitable location. The switch 32 can be connected by respective wiring 30 and an input adaptor to the computer 28. Reiterating from above, the computer 28 can have associated therewith and/or may be replaced by one or more programmable logic devices (PLDs) and/or application-specific integrated circuits (ASIC), as will be discussed in greater detail below. The unit 10 typically further includes a power supply unit (not shown) that supplies electrical power for the unit's electronic components, as will be understood by those of ordinary skill in the art.

Referring to FIG. 2, the housing 16 can include a circular rear panel 33 that is opaque to visible light and closes the rear of the housing interior. In the first embodiment, the front of the housings interior 18 is closed by a circular window 34 that forms the front face of the upper body 12. The window 34 is typically mounted to the front of the housing 16 so that the body's electronic components 20, 22, 24, 26, 28, 30 are substantially enclosed within the housing behind the window.

The window 34 can be a piece of glass, polymeric material, or other suitable material that is transparent or translucent with respect to visible light emitted by the light panels 20, 22. The light panels 20, 22 and an outer annular wall of the housing 16 can be concentrically arranged. The light panels 20, 22 can be flat, dimmable, color changing, light emitting diode (LED) light panels that have been cut or otherwise formed in an annular shape.

In the first embodiment, the inner periphery of the outer light panel 20 is slightly larger than the outer periphery of the inner outer light panel 22, and the light panels are arranged so that the outer light panel extends around, and is substantially coplanar with, the inner light panel. The light panels 20, 22 can be closely adjacent to, or in opposing face-to-face contact with, the inner surface of the window 34.

The window 34 can be translucent to visible light in manner that both: (i) allows the outward transmission therethrough of light emitted from the light panels 20, 22, and (ii) substantially hides the electronic components 20, 22, 24, 26, 28, 30 from view behind the window 34. Accordingly, FIG. 1 depicts that the electronic components 20, 22, 24, 26, 28, 30 are substantially unseen through the window 34.

Figure 3:
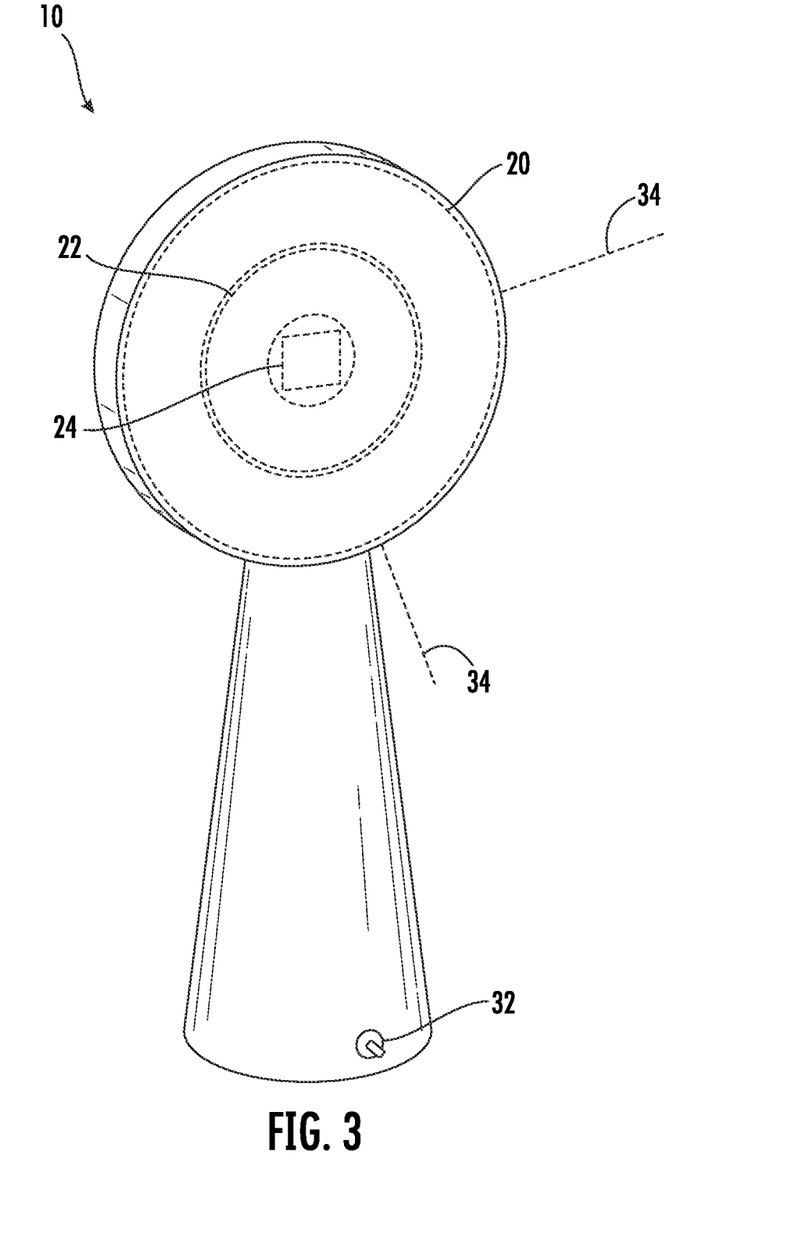
FIG. 3 is another front pictorial view of the unit of FIG. 1, wherein several features are schematically represented by dashed lines, in accordance with the first embodiment.

In contrast with FIG. 2, FIG. 3 schematically depicts the hidden light panels 20, 22 and detector 24 with dashed lines. Other dashed lines schematically represent the field of view 36 of the detector 24. In the example depicted in FIG. 3, the detector 24 is centrally located so that its field of view 36 extends through the central opening of the inner light panel 22. Alternatively, the detector 24 can be positioned less concentrically in the unit's upper body 12, or outside of the unit 10, as will be discussed in greater detail below.

It is believed that the detector 24 can be a pulsed wave doppler radar system ("radar apparatus") capable of detecting presence of a user in the field of view 36, distance to the user in the field of view, and motion of the user in the field of view. It is believed that radar apparatus 24 can detect and/or be used to determine at least the breathing rate of the user in the field of view 36. It is believed that radar apparatus 24 may also be able to detect and/or be used to determine: (i) the heartbeat of the user in the field of view, (ii) whether the user is sleeping or awake, and (iii) whether the user is in rapid eye movement (REM) sleep, non-REM sleep and/or the other stages of sleep.

In embodiments of the unit 10 in which the radar field of view 34 passes through the window 34, the window is typically constructed of material that is substantially transparent to, and minimally attenuates, electromagnetic signals transmitted and received by the radar apparatus 24. It is believed that the window may be constructed of polymeric material such as polyurethane and/or other suitable materials. It is believed that a suitable radar apparatus 24 is available from Novelda AS based in Norway, as products referred to as XeThru radar transceivers.

In the first embodiment, the radar apparatus 24 is configured for detecting (e.g., non-contact sensing) one or more indicators of the physiological state of the user, and outputting data representative of the indicators. The radar apparatus 24 and a first software module executed by the processor of the computer 28 can be cooperatively configured to identify one or more physiological conditions of the user. It is believed that a suitable first software module is available from Novelda AS based in Norway, as products referred to as XeThru software. A second software module executed by the processor of the computer 28 can access a computer database including a lookup table, or the like, to determine what actions, if any, are to be taken in response to the identified physiological condition(s) of the user, as will be discussed in greater detail below.

In the first embodiment, the unit 10 is configured for affecting the environment in which the user is located ("environment-affecting device"). In this regard, the unit 10 can have different modes of operation, examples of which are described in the following, in accordance with the first embodiment.

The first example unit 10 can function in an Awakening Mode, which seeks to help awaken the user by promoting alertness of the user, and a Sedating Mode, which seeks to help the user relax and fall asleep. In an example of an arrangement for facilitating the Awakening Mode and the Sedating Mode, the unit 10 can be arranged (e.g., positioned on a bedside table) so that the field of view 36 of the radar apparatus 24 is directed toward and encompasses, or at least partially encompasses, the user lying on top of a bed. For example, typically at least the users torso and head are in the radar's field of view 36. It is believed that electromagnetic signals transmitted and received by the radar apparatus 24 can pass through clothing, bed sheets, and blankets with substantially minimal attenuation.

A First Version of the Awakening Mode provided by the unit 10 stimulates the user by using a first color of light, for example white light, blue light, and/or orange light emitted (e.g., emitted continuously) from one or more of the light panels 20, 22. More specifically, the at least one switch 32, one or more light panels 20, 22, and a suitable processor (e.g., the computer 28, PLD, and/or ASIC) can be cooperatively configured to cause the unit 10 to operate in the Awakening Mode. The processor can receive a signal from the at least one switch 32 for initiating the Awakening Mode provided by the unit 10. In response to receiving the initiating signal from the at least one switch 32, the processor provides at least one signal that controls operation of at least one of the light panels 20, 22. In response to the signals from the processor, at least one of the light panels 20, 22 emits a first color of light, for example blue light, at a brightness that seeks to stimulate the user. The brightness of the light may increase over a period of time to reach a peak brightness in a predetermined period of time, for example several minutes, thirty minutes, an hour or another suitable time period. In another version of the Awakening Mode, the below-discussed Breathing Exercises are provided with blue light rather than amber, orange, or red light.

A First Version of the Sedating Mode provided by the unit 10 includes guiding the user through a diaphragmatic or deep breathing exercise (Breathing Exercise) using a second color of light, for example amber light emitted from the one or more light panels 20, 22. More specifically, the one or more light panels 20, 22 and a suitable processor (e.g., the computer 28, PLD, and/or ASIC) can be cooperatively configured to guide the user through the Breathing Exercise. The processor can receive a signal from, for example, the at least one switch 32 for initiating the Breathing Exercise. In response to receiving the initiating signal from the at least one switch 32 and/or from another suitable component, the processor provides signals that control operation of at least one of the light panels 20, 22. In response to the signals from the processor, at least one of the light panels 20, 22 emits light, for example amber light, at a brightness that changes through a time cycle that is serially repeated numerous times. For example, in each cycle the light's brightness fades in and out (e.g., increases and decreases), and the user follows his or her own breath to the light. In one specific example, in each cycle the light fades in and out based on the rhythm of 4 seconds inhale, hold for 6 seconds, and exhale for 8 seconds; and the cycles are repeated serially for thirty seconds. For each cycle, the emitted light can be orange during the inhale and hold portions of the cycle, and red during the exhale portion of the cycle.

In another specific example, each cycle can comprise, consist essentially of, or consist of: (i) increasing brightness of the light over a period of time (e.g., several seconds; a predetermined number of seconds; about four, five or six seconds; and/or an adjustable number of seconds) for signaling that the user inhale during the brightening; (ii) then optionally maintaining a peak brightness for a period of time (e.g., one or a few seconds) for signaling that the user pause her or his breathing; (iii) then decreasing brightness of the light and/or changing to a different (e.g., deeper) color hue over a period of time (e.g., several seconds; a predetermined number of seconds; about four, five or six seconds; and/or an adjustable number of seconds) for signaling that the user exhale during the dimming; and (iv) then optionally maintaining the lack of or least brightness for a period of time (e.g., one or a few seconds) for signaling that the user pause her or his breathing. For each cycle, the emitted light can be orange during both the inhale portion of the cycle and the immediately following pause portion of the cycle, and red during both the exhale portion of the cycle and the immediately following pause portion of the cycle.

The cycles can be serially repeated numerous times (e.g., a predetermined number of times, for example five to ten times; a predetermined period of time, for example thirty seconds, five minutes or ten minutes; and/or an adjustable number of times).

A Second Version of the Sedating Mode provided by the unit 10 can be like the First Version of the Sedating Mode except for variations noted and variations that will be apparent to those of ordinary skill in the art. In the Second Version of the Sedating Mode, a first of the light panels 20, 22 is operated to guide the breathing of the user through the Breathing Exercise as discussed above, and a second of the light panels 20, 22 is operated to indicate the present breathing of the user in real time, so that the user can compare the contrast between the light being emitted from the light panels in an effort to better control her or his breathing to follow the Breathing Exercise.

More specifically regarding the second of the light panels 20, 22 being operated to indicate the present breathing of the user in real time, the radar apparatus 24 is operatively associated with the processor (e.g., the computer 28, PLD, and/or ASIC) for providing signals to the processor that provide data indicative of the rate of breathing of the user. In response to receiving the data indicative of the user's breathing rate, the processor provides signals that control operation the second of the light panels 20, 22. In response to the signals from the processor, the second of the light panels 20, 22 emits light, for example amber light, at a brightness that follows the user's breathing in real time.

For providing an indication of the user's breathing in real time, (i) the brightness of the second of the light panels 20, 22 increases for signaling that the user is inhaling; (ii) then optionally the brightness of the second of the light panels 20, 22 may be maintained at a peak brightness for a period of time for signaling that the user has paused her or his breathing; (iii) then the brightness of the second of the light panels 20, 22 decreases over a period of time to signal exhalation by the user; and (iv) then optionally the brightness of the second of the light panels 20, 22 may be maintained in an off state or a reduced brightness for signaling that the user has paused her or his breathing.

The switch 32 can be a conventional rotary dial switch associated with the controller for allowing a user to select between any number of the above-discussed operational modes.

Figure 4:
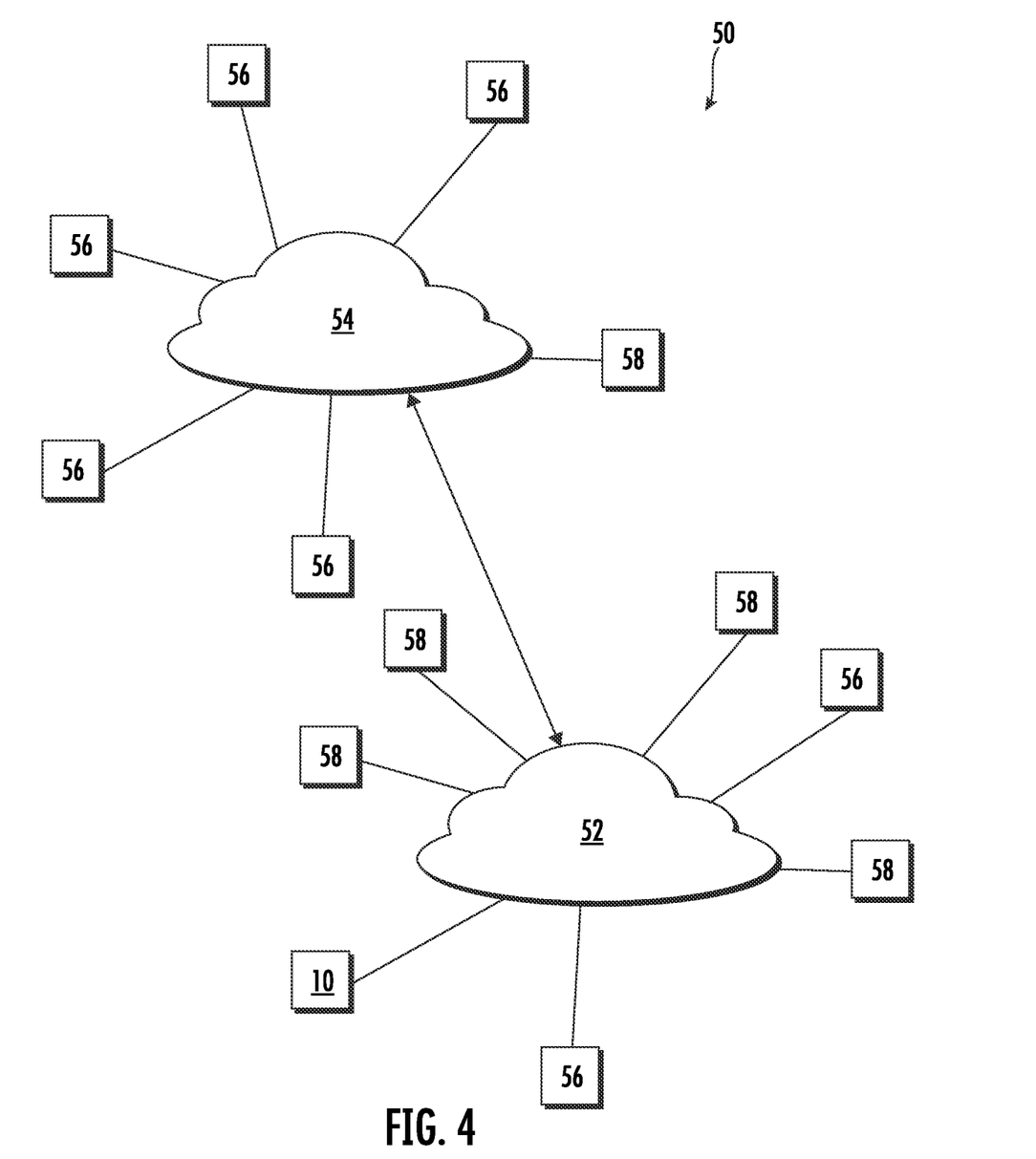
FIG. 4 is a block diagram of a system configured to detect and/or positively affect the physiological condition of a user, in accordance with a first embodiment of this disclosure.

A second embodiment of this disclosure can be like the above-discussed first embodiment, except for variations noted and variations that will be apparent to those of ordinary skill in the art. In accordance with the second embodiment, FIG. 4 depicts that the unit 10 is part of a networked system 50. The networked system 50 can include at least one unit 10; one or more networks communicatively connected to one another, for example a local area network 52 (e.g., a wireless local area network ("LAN")) and a wide area network 54 (e.g., the internet ("WAN")). The networks 52, 54 can be connected to numerous network-connected devices having a wide variety of different capabilities. For example, primary network-connected device 56 ("primary devices") can include smartphones; smartwatches; personal digital assistants; portable, tablet, or mobile computers; desktop computers; carputers; server computers (e.g., a web server for serving contents (e.g., web pages and sites) to the World Wide Web); and/or any other suitable computerized devices (e.g., one or more controllers for controlling operation of one or more secondary devices). As another example, the networks 52, 54 can be connected to secondary network-connected devices 58 ("secondary devices") that typically have at least some lesser capabilities as compared with the primary devices 56. For example, the secondary devices 58 may be at least partially controlled by way of a user interface and/or processor of one or more of the primary devices 56. In the example depicted in FIG. 4, each of the unit 10 and primary and secondary devices 56, 58 is one of the Internet of things.

In the second embodiment, the unit 10 can be one of the secondary devices 58, and each of, or at least some of, the secondary devices can be configured for affecting the environment in which the user is located ("environment-affecting devices"). Other examples of the environment-affecting secondary devices 58 include a network-connected thermostat, network-connected light, network-connected alarm clock, network-connected fan, network-connected diffuser, network-connected door lock, network-connected speakers, and any other suitable network-connected devices. It is believed each of a network-connected thermostat, a network-connected light, a network-connected alarm clock, a network-connected fan, a network-connected diffuser, a network-connected door lock, and a network-connected speaker are presently commercially available items that are not novel per se. Similarly, one or more of the primary devices 56 can be configured for affecting the environment in which the user is located ("environment-affecting devices").

In the second embodiment, the unit 10 can be communicatively coupled with one or more of the primary and secondary devices 56, 58 by way of one or more of the networks 52, 54, and/or one or more of the components or features of the unit 10 can be relocated from the unit 10 to one or more of the other primary and secondary devices 56, 58. As another example, rather than or in addition to the unit 10 including the radar apparatus 24, one or more of the primary and secondary devices 56, 58 can include the radar apparatus 24. As a more specific example, the unit 10 can be omitted from at least one version of the second embodiment.

In an example of an arrangement for facilitating the Awakening Mode, the Sedating Mode, and an Restless Sleep Mode that are provided by the system 50, the field(s) of view 34 of the system's one or more radar apparatuses 24 are directed toward and encompass, or at least partially encompass, the user lying on top of a bed. For example, typically at least the users torso and head are in the one or more fields of view 36. For example, a primary or secondary device 56, 58 including a radar apparatus 24 may be mounted to a wall or a headboard of the bed so that the radar's field of view 36 is inclined downwardly toward the top of the bed. As another example, a primary or secondary device 56, 58 including a radar apparatus 24 may be mounted to a ceiling above the bed so that the radar's field of view 36 is directed downwardly toward the top of the bed, and/or a primary or secondary device 56, 58 including a radar apparatus 24 may be configured in any other suitable manner so that the radar's field of view 36 sufficiently encompasses at least a portion of the user. As a further example, one or more of the primary and secondary devices 56, 58 may store a variety of data originating from the radar apparatus(es) 24 in a databank, and that data may be used for a variety of different proposes. For example, doctors may access the data for the purpose of conducting sleep studies and/or for other suitable purposes.

It is believed that the data from the one or more radar apparatuses 24 can processed by one or more of the processors of one or more of the primary or secondary devices 56, 58 to monitor the user throughout their sleeping in order to quantify the user's sleep over time, including identifying REM sleep, non-REM sleep, Stage 1 sleep (e.g., the transitional phase), Stage 2 sleep (e.g., a non-REM phase and lighter stage of sleep), Stages 3 and 4 of sleep (e.g., non-REM phases of deep sleep), Stage 5 sleep (e.g., REM sleep), and any restless sleeping experienced by the user.

For example, restless sleeping can be described as being sleeping characterized by a relatively high movement rate of the user, relatively shallow breathing by the user, and/or relatively quick breathing by the user. As another example, restless sleeping can include a relatively rapid heart rate (e.g., pulse) of the user, a relatively high movement rate of the user, relatively shallow breathing by the user, and/or relatively quick breathing by the user.

The system 50 can have the modes of operation discussed above for the first embodiment, plus additional modes of operation, examples of which are described in the following, in accordance with the second embodiment. The initiating performance of, ceasing performance of, setting the parameters of and/or adjusting the parameters of each of the modes of operation of one or more of the respective environment-affecting devices 10, 56, 58 of the second embodiment can be at least partially controlled: (i) by way of a user using the user interface of a respective device 56, 58 executing a respective software application; (ii) by way of a user using a user interface of a respective device 56, 58 having a web browser interacting with a web site served by a respective primary device 56; (iii) and/or in response to receiving instructions over one or more of networks 52, 54 from one or more respective processors (e.g., computer processor, PLD, and/or ASIC) of one or more of the devices 56, 58.

A Second Version of the Awakening Mode provided by the system 50 can be like the above-discussed First Version of the Awakening Mode, except for variations noted and variations that will be apparent to those of ordinary skill in the art. In the Second Version of the Awakening Mode, responsive to instructions from at least one processor (e.g., computer processor, PLD, and/or ASIC) of a respective device 56, 58:

one or more of the light panels 20, 22 can operate to illuminate the environment of the user as in the above-discussed First Version of the Awakening Mode;

the network-connected, environment-affecting thermostat 58 can operate to cause an associated heating, ventilation, and/or air conditioning (HVAC) unit to adjust (e.g., increase) the temperature of the environment of the user;

the network-connected, environment-affecting light 58 can turn on or otherwise brighten the environment of the user;

the network-connected, environment-affecting alarm clock 58 can initiate emission of an audible sound (e.g., an alarm sound or music intended to promote alertness of the user) in the environment of the user;

operation of the network-connected, environment-affecting fan 58 positioned in, or otherwise affecting, the environment of the user can be slowed or ceased;

the network-connected, environment-affecting diffuser 58 can initiate diffusion of aromatic oils or other suitable substances (e.g., the smell of peppermint or another suitable stimulating smell) into the environment of the user (e.g., it is believed that a user can learn more quickly when introducing the same smells while sleeping, that were present when they learned something);

one or more of the primary devices 56 (e.g., smartphones; smartwatches; personal digital assistants; portable, tablet, or mobile computers; desktop computers; and/or the like) in the environment of the user can be turned on or otherwise activated;

any night time light setting (which reduces the amount of blue light displayed) for the display screen of one or more of the primary devices 56 (e.g., smartphones; smartwatches; personal digital assistants; portable, tablet, or mobile computers; desktop computers; and/or the like) in the environment of the user can be turned off;

the network-connected, environment-affecting speakers 58 can initiate or adjust the emission of an audible sound (e.g., music intended to promote alertness of the user) in the environment of the user; and/or one or more other suitable network-connected devices 56, 58 can be operated or operatively adjusted in a manner that affects the environment in which the user is located in a manner that seeks to aid in the awakening of/promote alertness of the user.

A Third Version of the Sedating Mode provided by the system 50 can be like the above-discussed First and Second Version of the Sedating Modes, except for variations noted and variations that will be apparent to those of ordinary skill in the art. In the Third Version of the Sedating Mode, responsive to instructions from at least one processor (e.g., computer processor, PLD, and/or ASIC) of a respective device 56, 58:

one or more of the light panels 20, 22 can operate to provide the Breathing Exercise in the environment of the user as in the above-discussed First and Second Version of the Sedating Modes;

the network-connected, environment-affecting thermostat 58 can operate to cause an associated HVAC unit to adjust (e.g., decrease) the temperature of the environment of the user;

the network-connected, environment-affecting light 58 can turn off or otherwise dim the environment of the user;

operation of the network-connected, environment-affecting fan 58 positioned in, or otherwise affecting, the environment of the user can be turned on or sped up;

the network-connected, environment-affecting diffuser 58 can initiate diffusion of aromatic oils or other suitable substances (e.g., the smell of lavender or another suitable relaxing or sedating smell) into the environment of the user;

one or more of the primary devices 56 (e.g., smartphones; smartwatches; personal digital assistants; portable, tablet, or mobile computers; desktop computers; and/or the like) in the environment of the user can be turned off or otherwise manipulated;

the night time light setting (which reduces the amount of blue light displayed) for the display screen of one or more of the primary devices 56 (e.g., smartphones; smartwatches; personal digital assistants; portable, tablet, or mobile computers; desktop computers; and/or the like) in the environment of the user can be turned on;

the network-connected, environment-affecting speakers 58 can initiate or adjust the emission of an audible sound (e.g., music intended to relax or sedate the user) in the environment of the user;

one or more network-connected door locks 58 can operate to lock one or more doors associated with the environment of the user; and/or one or more other suitable network-connected devices 56, 58 can be operated or operatively adjusted in a manner that affects the environment in which the user is located in a manner that seeks to aid in the relaxation or sedation of the user.

In the Restless Sleep Mode provided by the system 50, responsive to instructions from at least one processor (e.g., computer processor, PLD, and/or ASIC) of a respective device 56, 58:

one or more of the light panels 20, 22 can operate to provide the Breathing Exercise in the environment of the user as in the above-discussed First and Second Version of the Sedating Modes;

the network-connected, environment-affecting thermostat 58 can operate to cause an associated HVAC unit to adjust (e.g., decrease) the temperature of the environment of the user;

the network-connected, environment-affecting light 58 can turn off or otherwise dim the environment of the user;

operation of the network-connected, environment-affecting fan 58 positioned in, or otherwise affecting, the environment of the user can be turned on or sped up;

the network-connected, environment-affecting diffuser 58 can initiate diffusion of aromatic oils or other suitable substances (e.g., the smell of lavender or another suitable relaxing or sedating smell) into the environment of the user;

one or more of the primary devices 56 (e.g., smartphones; smartwatches; personal digital assistants; portable, tablet, or mobile computers; desktop computers; and/or the like) in the environment of the user can be turned off or otherwise manipulated;

the night time light setting (which reduces the amount of blue light displayed) for the display screen of one or more of the primary devices 56 (e.g., smartphones; smartwatches; personal digital assistants; portable, tablet, or mobile computers; desktop computers; and/or the like) in the environment of the user can be turned on;

the network-connected, environment-affecting speakers 58 can initiate or adjust the emission of an audible sound (e.g., music intended to relax or sedate the user) in the environment of the user; and/or one or more other suitable network-connected devices 56, 58 can be operated or operatively adjusted in a manner that affects the environment in which the user is located in a manner that seeks to aid in the relaxation or sedation of the user.

At least partially reiterating from above, the modes of operation of the present disclosure can be initiated: (i) by way of a user using the user interface of a respective device 56, 58 executing a respective software application; (ii) by way of a user using a user interface of a respective device 56, 58 having a web browser interacting with a web site served by a respective primary device 56; (iii) and/or in response to receiving instructions over one or more of networks 52, 54 from one or more respective processors (e.g., computer processor, PLD, and/or ASIC) of one or more of the devices 56, 58. For example, the at least one radar apparatus 24 of a respective device 56, 58 can utilizes non-contact sensing to determine one or more indicators of the physiological condition of the user, so that the radar apparatus outputs data representative of the indicators, and the data is received by at least one processor (e.g., computer processor, PLD, and/or ASIC) of a respective device 56, 58. The at least one processor can compare the data to various thresholds and/or otherwise suitably analyze the data, and responsively provide instructions to the respective device(s) 56, 58 for facilitating the respective mode of operation. For example, an Awakening Mode of operation of the system 50 can be initiated in response to the at least one radar apparatus 24 and the at least one processor cooperatively detecting that the user in the radar's field of view 36 has reached the end of Stage 5 sleep and/or other suitable condition(s) exist. As another example, a Sedating Mode of operation of the system 50 can be initiated in response to the at least one radar apparatus 24 and the at least one processor cooperatively detecting that the user has lain down on a bed in the radar's field of view 36 and/or other suitable condition(s) exist. As a further example, a Restless Sleep Mode of operation of the system 50 can be initiated in response to the at least one detector (e.g., the radar apparatus 24 and/or other suitable detector(s)) and the at least one processor cooperatively detecting that the user has a relatively high movement rate, relatively shallow breathing, relatively quick breathing, a relatively rapid heart rate (e.g., pulse), and/or other suitable condition(s) exist.

Figure 5:
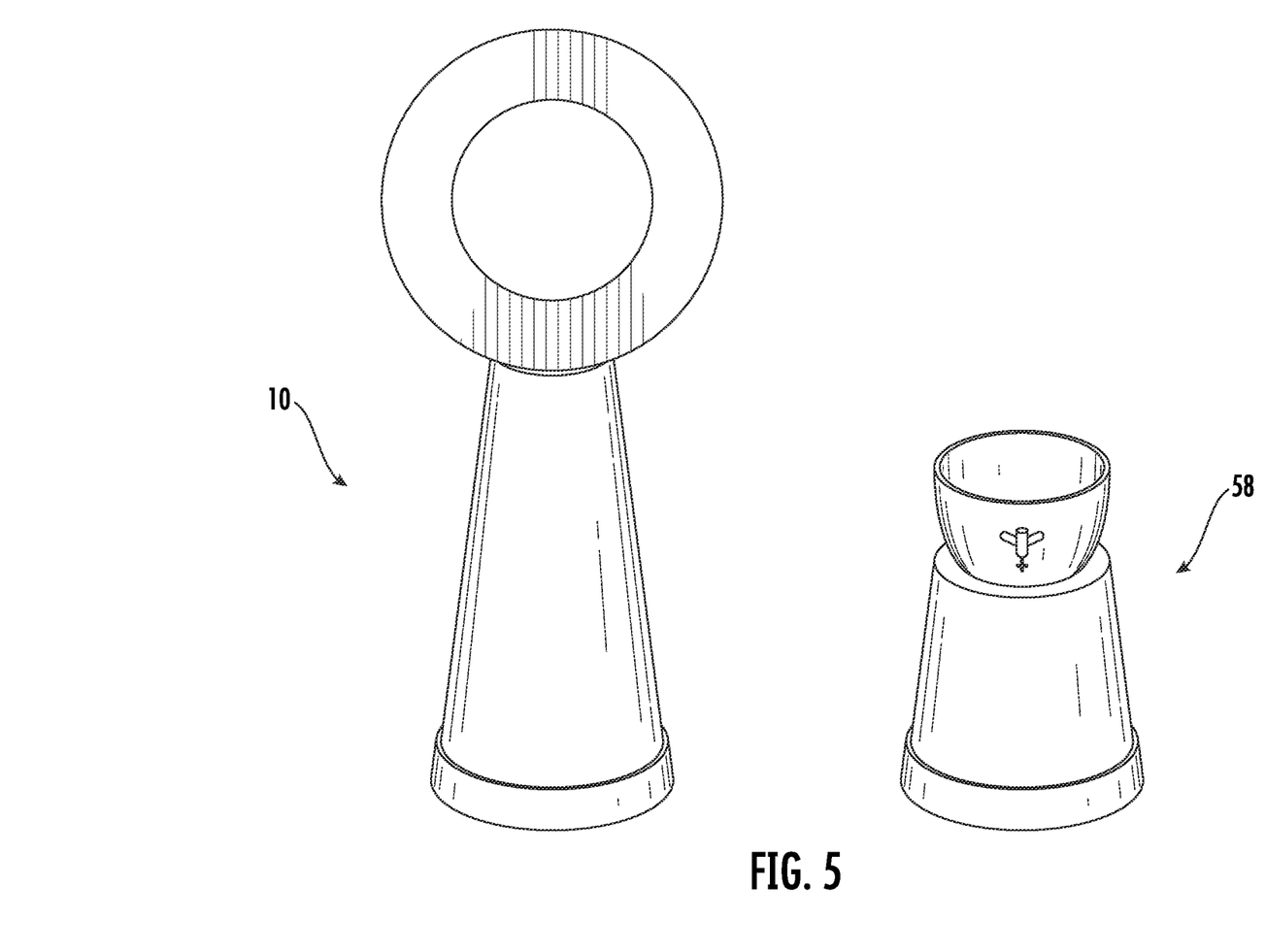
FIG. 5 is a front pictorial view of the unit of FIG. 1 in combination with a diffuser, in accordance with an embodiment of this disclosure.

As an example, FIG. 5 depicts the unit 10 and diffuser 58 positioned closely to one another. The unit 10 and diffuser 58 may be provided together, as part of a kit or system configured to detect and/or positively affect the physiological condition of a user. The unit 10 can be communicatively coupled with the diffuser 58, for example by way of one or more of the networks 52, 54 and/or in any other suitable manner. As examples of various implementations, there can be a close physical connection between the unit 10 and diffuser 58. In one specific example, the unit 10 can be reconfigured to physically include the diffuser 58 and vice versa, so that the unit 10 and diffuser 58 are both integral parts of a single article of manufacture that includes the features of both the unit 10 and diffuser 58.

Each of the primary and secondary devices 56, 58, 10 can include one or more of the components described below with reference to a representative one of the primary or secondary devices. The primary or secondary device can include electronic circuits forming a processor communicatively coupled to memory. The processor is typically communicatively coupled to other components of the primary or secondary device via a system bus and/or interface circuit. Similarly, the other components (e.g., the memory) of the primary or secondary device may each be communicatively coupled to other components of the primary or secondary device via the system bus and/or the interface circuits. Other embodiments of system bus architecture providing for efficient data transfer and/or communication between the components of the primary or secondary device may be also be employed.

The primary or secondary device typically further includes, or is otherwise communicatively coupled to, a network communication adapter (see, e.g., the network communication adapter 26 in FIG. 2) that facilitates communications (e.g., the exchange of messages) between the primary or secondary device and other nodes of the respective network, which communications may be further communicated from the respective network to other networks communicatively connected to the respective network. Messages, in the context of this disclosure, include any intra-network or inter-network communications.

The primary or secondary device's processor is typically communicatively coupled to a user interface. The user interface typically includes a visual display (e.g., display screen). The visual display may be a touch screen, which is capable of displaying visual information and receiving tactile commands from a user. In addition to the visual display, the user interface may also include one or more speakers, buttons, keyboards, mice, and/or microphones.

Typically, the processor (e.g., computer processor, microprocessor, processing unit) of the primary or secondary device is configured to execute instructions and to carry out operations associated with the primary or secondary device. For example, using instructions retrieved from the memory (e.g., a memory block, memory store), the processor may control the reception and manipulation of input and output data between components of the primary or secondary device. The primary or secondary device may include multiple processors for increased processing power. The processors may be in the form of a distributed processor using more than one computer, for example one or more server computers (e.g., a web server for serving contents (e.g., web pages and sites) to the World Wide Web), and/or any other suitable computerized devices.

The processor typically operates with an operating system to execute computer code and produce and use data to support the functioning of the primary or secondary device. The operating system generally is computer code (e.g., software) that manages the primary or secondary device's hardware resources and provides common services for computer applications being executed by the processor. The operating system may be a distributed operating system managing a group of physically independent computers in such a way as to allow them to perform cooperatively and collectively as a single computer. The operating system, other computer code (e.g., program modules, applications), and data may reside within the memory that is operatively coupled to the processor. The processor may be in the form of a distributed processor using more than one computer, for example one or more server computers (e.g., a web server for serving contents (e.g., web pages and sites) to the World Wide Web), and/or any other suitable computerized devices.

It will be appreciated by a person of ordinary skill in the art that the functions performed by the processor in response to computer code may be alternatively implemented in hardware (e.g., computer hardware) or a combination of hardware and software. For example, one or more programmable logic devices (PLDs) and/or application-specific integrated circuits (ASIC) could be used to carry out the functions of any of the primary or secondary device's program modules.

The memory generally provides a place to store computer code and data that are used by the primary or secondary device. The memory may include Read-Only Memory (ROM), Random-Access Memory (RAM), a hard disk drive, and/or other non-transitory storage media. A basic input/output system (BIOS) containing the basic routines that help to transfer information between components of the primary or secondary device, such as during start-up, is stored in ROM. The primary or secondary device's RAM typically contains data and/or program modules that are immediately accessible to and/or presently operated on by the processor.

In some embodiments, the memory may house a databank, which is a database for storing data in an organized manner for later searching (e.g., querying) and retrieval. Typically, the databank is housed (e.g., stored) on at least one hard disk drive component of memory. One of ordinary skill in the art will appreciate that other computer storage media may be utilized for housing the databank without departing from the scope of the invention. For example, the databank may be stored on any combination of hard disk drives, memory chips, solid state drives, optical drives, and the like. One of ordinary skill in the art will also recognize that the databank may be housed on multiple, distributed storage devices.

The data may be structured in the databank in any suitable manner, including the following data structure forms: relational database, object-oriented database, hierarchical database, lightweight director access protocol (LDAP) director, object-oriented-relational database, etc. The databank may conform to any database standard, or may conform to a non-standard, private specification. The databank may be implemented using, for example, any number of commercially-available database products, including SQL Server and Access from Microsoft Corporation, Oracle® from Oracle Corporation, Sybase® from Sybase, Incorporated, etc.

The operating system, other computer code, and data may also reside on a removable non-transitory storage medium that is loaded or installed onto primary or secondary device when needed. Exemplary removable non-transitory storage media include CD ROM, PC-CARD, memory card (e.g., flash memory card), floppy disk, and/or magnetic tape. The operating system, other computer code, and data may reside upon more than one computer, for example one or more server computers (e.g., a web server for serving contents (e.g., web pages and sites) to the World Wide Web), and/or any other suitable computerized devices.

Reiterating from above, it is within the scope of this disclosure for one or more of the terms "substantially," "about," "approximately," and/or the like, to qualify each of the adjectives and adverbs of the foregoing disclosure, for the purpose of providing a broad disclosure. As an example, it is believed that those of ordinary skill in the art will readily understand that, in different implementations of the features of this disclosure, reasonably different engineering tolerances, precision, and/or accuracy may be applicable and suitable for obtaining the desired result. Accordingly, it is believed that those of ordinary skill will readily understand usage herein of the terms such as "substantially," "about," "approximately," and the like.

In the specification and drawings, examples of embodiments have been disclosed. The present invention is not limited to such exemplary embodiments. The use of the term "and/or" includes any and all combinations of one or more of the associated listed items. Unless otherwise noted, specific terms have been used in a generic and descriptive sense and not for purposes of limitation.

The invention claimed is:

1. An apparatus for affecting the physiological condition of a user, the apparatus comprising:
   a housing having an interior space;
   at least one light source positioned in the interior space;
   a window mounted to the housing and configured to allow light from the at least one light source to pass through the window and outwardly from the housing;
   at least one sensor having a field of view that extends outwardly from the window and outwardly from the housing; and
   a controller in communication with the at least one light source and the at least one sensor;
   wherein the controller and the at the least one light source are cooperatively configured to control light emitted from a first portion of the at least one light source so that brightness of the light emitted from the first portion changes through a time cycle that is serially repeated for guiding breathing of a user positioned at least partially in the field of view of the at least one sensor:
   wherein the controller and the at least one sensor are cooperatively configured to detect at least one physiological condition of the user indicating present breathing rate; and
   wherein the controller and the at the least one light source are cooperatively configured to control, during the brightness of the light from the first portion changing through the time cycle, light emitted from a second portion of the at least one light source indicating the present breathing rate of the user in real time, wherein color of the light emitted from the second portion is different than color of the light emitted from the first portion through the time cycle.

2. The apparatus according to claim 1, further comprising at least one switch in communication with the controller and configured to allow the user to select between at least a first mode and a second mode.

3. The apparatus according to claim 1, wherein the controller is configured to control the at least one light source in response to signals from the at least one sensor.

4. The apparatus according to claim 3, comprising a pulsed wave doppler radar system, wherein the at least one sensor is part of the pulsed wave doppler radar system.

5. The apparatus according to claim 3, wherein the at least one sensor is positioned in the interior space of the housing, and the at least one sensor is configured to have a field of view that extends through the window.

6. The apparatus according to claim 3, wherein the at least one light source comprises a first light source and a second light source.

7. The apparatus according to claim 1, further comprising a diffuser configured to diffuse at least one substance into the user's environment, wherein the controller is in communication with the diffuser and configured to control operation of the diffuser.

8. The apparatus according to claim 1, wherein the controller and the at least one light source are cooperatively configured so that color of the light changes through a time cycle that is serially repeated for guiding breathing of the user.

9. The apparatus according to claim 1, wherein the at least one light source comprises a substantially concentric light panels.

10. The apparatus according to claim 1, wherein the at least one light source comprises a light emitting diode light panel.

11. The apparatus according to claim 9, wherein:
the light emitting diode light panel is a first light emitting diode light panel; and
the at least one light source further comprises a second light emitting diode light panel extending at least partially around the first light emitting diode light panel.

12. A system for detecting and affecting the physiological condition of a user, the system comprising:
at least one non-contact sensor configured to detect at least one physiological condition indicating present breathing rate of a user;
a device configured for affecting the user's environment, the device comprising:
a housing having an interior space;
at least one light source positioned in the interior space; and
a window mounted to the housing and configured to allow light from the at least one light source to pass through the window and outwardly from the housing; and
at least one controller configured to communicate with and to control operation of both the at least one sensor and the device;
wherein the at least one controller is configured to:
control light emitted from a first portion of the at least one light source so that brightness of the light emitted from the first portion changes through a time cycle that is serially repeated for guiding breathing of the user;
detect, via signals received from the at least one sensor, the at least one physiological condition indicating present breathing rate of the user; and
during the brightness of the light from the first portion changing through the time cycle, control light emitted from a second portion of the at least one light source to indicate the present breathing rate of the user in real time, wherein color of the light emitted from the second portion is different than color of the light emitted from the first portion through the time cycle.

13. The system according to claim 12, comprising a pulsed wave doppler radar, wherein the at least one sensor is part of the pulsed wave doppler radar.

14. The system according to claim 12, further comprising a diffuser configured to diffuse at least one aromatic oil into the user's environment, wherein the at least one controller is in communication with the diffuser and configured to control operation of the diffuser.

15. The system according to claim 12, wherein:
the at least one controller is a network-connected controller,
the system further comprises a network-connected device including a user interface and configured to allow a user to control operation of the network-connected controller by way of at least the internet.

16. The system according to claim 12, wherein the at least one light source comprises a light emitting diode panel.

17. The system according to claim 16, wherein the at least one sensor is positioned in the interior space of the housing, and the at least one sensor is configured to have a field of view that extends through the window.

18. The system according to claim 16, wherein:
the light emitting diode panel is a first light emitting diode panel; and
the at least one light source further comprises a second light emitting diode light panel extending at least partially around the first light emitting diode light panel.

19. The system according to claim 18, wherein:
the first light emitting diode panel, the second light emitting diode panel, and an outer annular wall of the housing are concentrically arranged;
an inner periphery of the second light emitting diode panel is larger than an outer periphery of the first light emitting diode panel; and
the first light emitting diode panel and the second light emitting diode panel are in opposing face-to-face contact with an inner surface of the window.

20. The apparatus according to claim 11, wherein:
the first light emitting diode panel, the second light emitting diode panel, and an outer annular wall of the housing are concentrically arranged;
an inner periphery of the second light emitting diode panel is larger than an outer periphery of the first light emitting diode panel; and
the first light emitting diode panel and the second light emitting diode panel are in opposing face-to-face contact with an inner surface of the window.

* * * * *